United States Patent [19]

Jacquier et al.

[11] Patent Number: 5,138,037
[45] Date of Patent: * Aug. 11, 1992

[54] PROCESS FOR PREPARING PEPTIDE SYNTHONS

[75] Inventors: Robert Jacquier, Montpellier; Jean Verducci, Baillargues; Virginie Pevere, Montpellier, all of France

[73] Assignee: Rhone-Poulenc Chimie, Cedex, France

[*] Notice: The portion of the term of this patent subsequent to Dec. 31, 2008 has been disclaimed.

[21] Appl. No.: 664,519

[22] Filed: Mar. 5, 1991

Related U.S. Application Data

[63] Continuation of Ser. No. 188,415, Apr. 29, 1988, abandoned.

[30] Foreign Application Priority Data

Nov. 6, 1987 [FR] France .................. 87 15398

[51] Int. Cl.$^5$ .......................... C07K 3/00; C07K 3/04
[52] U.S. Cl. .................................. 530/335; 530/333; 530/334; 530/338
[58] Field of Search ............... 530/334, 335, 338, 333

[56] References Cited

U.S. PATENT DOCUMENTS 4,725,645 2/1988 Anteunis et al. .................. 530/334

FOREIGN PATENT DOCUMENTS 0289353 11/1988 European Pat. Off. ............ 530/334

OTHER PUBLICATIONS

Fournier, A., et al. Int. J. Peptide Protein Res., 31:86–97, 1988.
Vanfleteren, L., et al., Bull. Soc. Chim. Belg., 97:505–517, 1988.
Tung, R. D., et al., J. Org. Chem., 51:3350–3354, 1986.
Le-Nguyen, D., et al., J. Chem. Soc. Perkin Trans., I:1915–1919, 1987.
Kricheldorf, H., Liebigs Ann. Chem., 763:17–38, 1972.
Ramage, R., Peptides, Proc. Eur. Pept. Symp., 17th, Meeting Date 1982; 157–162, 1983.
Miyazawa et al., Peptide Chemistry, 1982, pp. 69–74.
Arnold et al., Synthetic Reactions of Dimethylformamide XIV., 1961.

Primary Examiner—Howard E. Schain
Assistant Examiner—Susan M. Perkins
Attorney, Agent, or Firm—Finnegan, Henderson, Farabow, Garrett and Dunner

[57] ABSTRACT

The present invention relates to a process for preparing optically active synthons, in which an oxygen-silylated amino acid or peptide having a protected nitrogenous group, is activated by a non-coordinated halogenated phosphorus derivative and is condensed with an N-silyl amino acid or peptide in which the acid group is protected.

18 Claims, No Drawings

PROCESS FOR PREPARING PEPTIDE SYNTHONS

This application is a continuation of application Ser. No. 188,415, filed Jul. 29, 1988, now abandoned.

BACKGROUND OF THE INVENTION

The present invention relates to a process for preparing peptide synthons. It relates more especially to a new method of a non-racemizing peptide synthesis.

It is known from certain specialized works, such as, for example, The Peptides, Vol. 1, Academic Press (1979) or Principles of Peptide Synthesis, Springer (1984), to carry out peptide syntheses by condensing a peptide chain in which the acid terminus is activated (E) and the amine terminus is protected (P) with another peptide chain in which only the acid terminus is esterified. This synthesis is carried out in the presence of an organic base which permits neutralization of the leaving group (EOH) which is in most cases acidic. This synthesis is performed by the following reactions:

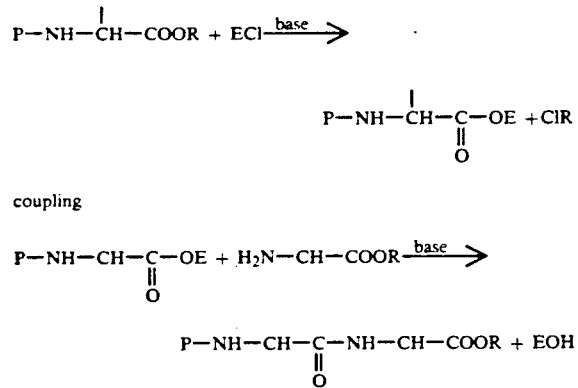

coupling

The base used, irrespective of its nature, causes substantial racemization of the peptide unit, either during the activation step or during the condensing or coupling step.

It is well known in peptide synthesis that most peptides are active only under a single diastereoisomeric form. Racemization causes a loss of activity of the products obtained after the condensation. This racemization is very detrimental to the use of the peptides because the chirally active starting materials used are often very expensive. Since the peptides are used in the pharmaceutical industry, which sets stringent analytical standards, the peptides must be purified if their synthesis produces a mixture of diastereoisomers. This purification is very costly.

As a result, industry has been seeking for a long time chemical processes which compete with the processes of extraction from natural products. Industry has sought active peptides of well defined chiral purity at a cost capable of competing with the extraction processes.

It is known, for example, to prepare peptides while inhibiting racemization to a maximum by the use of activating agents such as dicyclohexylcarbodiimide (DCC) and additives such as:
N-hydroxysuccinimide,
1-hydroxybenzotriazole,
N-hydroxy-5-norbornene-2,3-dicarboximide.

It is generally known to condense, without excessive racemization, amino acids which are N-protected by urethane groups. This condensation is performed by a synthesis technique that enables amino acids to be added to a peptide one by one. On the other hand, when the amine group is substituted by an acyl group as disclosed by Miyazawa, Yamada and Kuwata, Peptide Chemistry 69 (1982) or it forms part of a peptide chain, the degree of racemization is no longer insignificant and can reach 25%.

It is also known, from European Patent No. 184,243, to prepare silyl derivatives of amino acids or peptides using trialkylcyanosilanes, and then to couple these silyl derivatives with activated amino acids or peptides. During the silylation, there is a liberation of hydrocyanic acid, which is so toxic that it has led to the exclusion of this process from all industrial programs. Moreover, the activating agents used in the above-mentioned patent cannot be used on peptide fragments without the occurrence of substantial racemization.

Consequently, the degree of racemization varies with the activated amino acid, the protective group, the activating reagent and the conditions of the activation reaction. Particularly, the degree of racemization can be total when a acyl type protective group is used.

SUMMARY OF THE INVENTION

The present invention makes it possible to solve the problems remaining in the prior art. The present process can, by a chemical method using starting materials of low cost, produce a peptide synthon possessing a chiral purity as high as equal to or greater than 99% on condensing or coupling. This chiral purity can be obtained, for example, by coupling valine with another valine. Under experimental conditions not in accord with the present invention, the coupling of valine with valine, for example, when activated with (i) DCC and an additive, (ii) pivaloyl chloride and a tertiary amine, or (iii) N,N'-bis(2-oxo-3-oxazolidinyl) phosphinyl chloride (BOP-Cl) and tertiary amine, leads to a not insignificant racemization.

The present invention provides a process for preparing an optically active peptide synthon. In particular, the process can provide a substantially optically pure peptide synthon. In the first step, an oxygen-silyl derivative of a peptide or an amino acid in which the nitrogenous group is protected is prepared. In the second step, the oxygen-silyl peptide or amino acid is activated by a halogenated phosphorus derivative. In a third step, the activated peptide or amino acid is condensed with an amino acid or peptide having a protected acid group and an N-silyated amine group.

The present invention, hence, makes it possible to avoid any involvement of a base, especially in the activation step and in the condensing step. This is especially advantageous when the silylated component contains more than one amino acid.

These and other features and advantages of the present invention will be made more apparent from the following description of the preferred embodiment.

DETAILED DESCRIPTION OF THE PREFERRED EMBODIMENT

Preferably, the overall reaction of the present invention can be represented schematically by the following reactions:

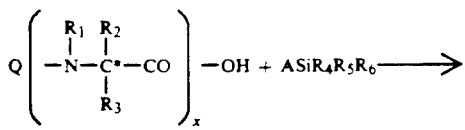  (A)

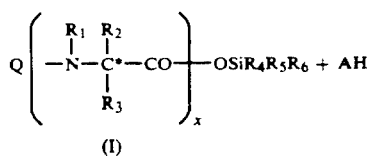

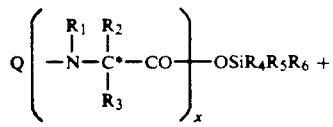  (B)

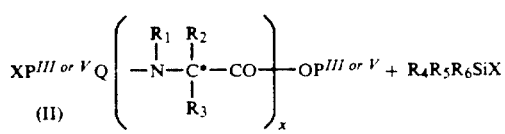

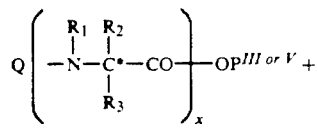  (C)

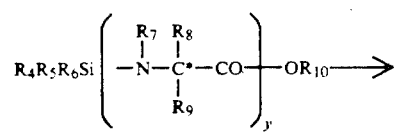

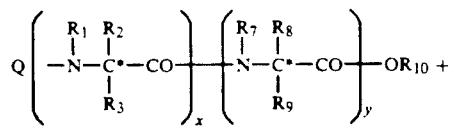

A in these formulae denotes chlorine or a group

in which:

R' denotes hydrogen or an alkyl group $C_nH_{2n+1}$ with n being an integer between 1 and 4;

R" denotes an alkyl group $C_nH_{2n+1}$ with n being an integer between 1 and 4 or a trialkylsilyl group in which the alkyl group contains 1 to 4 carbon atoms;

R' and R" can also form an alkylsilyloxyalkylidene group, and in particular the group

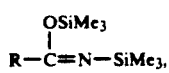

with R being a trifluoromethyl group.

Q in these formulae is one of the protective groups for the N-terminal amine group used in the methods known in the prior art, such as Gross and Meienhofer, The Peptides, Vol. 3, Academic Press (1981). By way of non-limiting examples, Q can be a t-butyloxycarbonyl (BOC), benzyloxycarbonyl (Z), fluorenylmethyloxycarbonyl (Fmoc), benzoyl, trifluoroacetyl or formyl group.

$R_1$ and $R_7$ are either a hydrogen or a methyl group.

$R_2$ and $R_8$ may be chosen from the following substituents: hydrogen, alkenyl groups, alkyl groups having the formula $C_nH_{2n+1}$, either linear or branched, with n possessing integral values between 1 and 4, benzyl groups, or one of the groups included in the non-limiting list appearing below:

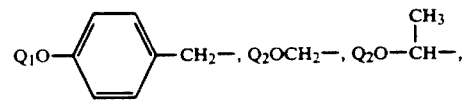

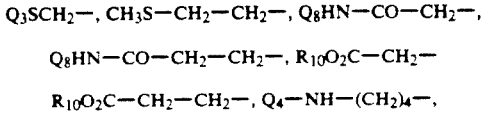

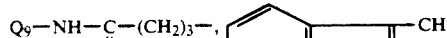

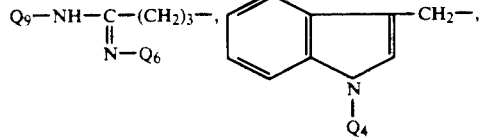

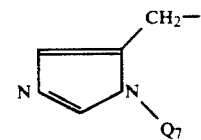

in which $Q_1$, $Q_2$, $Q_3$, $Q_4$, $Q_5$, $Q_6$, $Q_7$ and $Q_8$ are protective groups for the side chains, used in the methods disclosed in Gross and Meienhofer, The Peptides, vol. 3, Academic Press (1981). By way of non-limiting examples, $Q_1$ can be a benzyl, 2-bromobenzyl or 2,6-dichlorobenzyl group; $Q_2$ a benzyl or t-butyl group; $Q_3$ a benzyl, t-butyl, trityl, acetamidomethyl or benzamidomethyl group; $Q_4$ a trifluoroacetyl, t-butyloxycarbonyl or benzyloxycarbonyl group; $Q_5$ can be a nitro, p-methoxybenzenesulfonyl or mesitylenesulfonyl group when $Q_6$=H, or alternatively $Q_5$ and $Q_6$ can simultaneously consist of an adamantyloxycarbonyl group; $Q_7$ can be a phenacyl, benzyloxymethyl or t-butoxymethyl group; and finally $Q_8$ can be a benzhydryl, dimethoxybenzhydryl or xanthydryl group.

$R_3$ and $R_9$ are chosen from the following substituents: hydrogen or an alkyl group $C_nH_{2n+1}$ with n being an integer between 1 and 4.

$R_1$ with $R_2$ or $R_7$ with $R_8$ can also form a cyclopolymethylene chain containing 2 to 5 carbon atoms. The carbon atoms to which the substituents $R_2$ and $R_8$ are attached possess the L or D configuration. They are asymmetric (*) except when $R_2=R_3$ and $R_8=R_9$.

In the formula, x and y are integers between 1 and 15.

$R_4$, $R_5$ and $R_6$ are chosen from hydrogen and alkyl groups $C_nH_{2n+1}$, with n being an integer between 1 and 4, on condition that these three substituents are not simultaneously hydrogen atoms.

$R_{10}$ is one of the protective groups of the C-terminal acid group and of the side chain acid groups used in the methods disclosed in Gross and Meienhofer, The Peptides, Vol. 3, Academic Press (1981). By way of non-limiting examples, $R_{10}$ may be methyl, ethyl, phenyl, benzyl or t-butyl groups.

Preferably, the non-coordinated halogenated phosphorus derivative is a phosphorus-containing reagent $XP^{III\ or\ V}$ that is chosen from the derivatives of phosphorus in the oxidation state III or V, and in particular from:

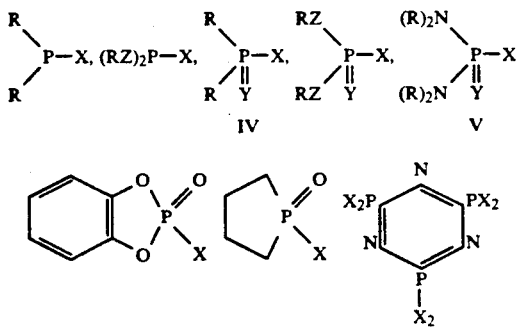

in which:

X is a chlorine or a bromine;

R is an alkyl group $C_nH_{2n+1}$, with n being an integer between 1 and 4, a phenyl group, or a 2-oxo-3-oxazolidinyl group; and Z and Y are independently oxygen or sulfur atoms.

Preferably, the phosphorous-containing reagent $XP^{III\ or\ V}$ is diphenylphosphinyl chloride (Dpp-Cl) of formula IV having $R=C_6H_5$, $Y=O$, $X=Cl$ or N,N'-bis(2-oxo-3-oxazolidinyl)phosphinyl chloride (BOP-Cl) of formula IV in which

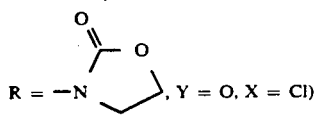

Under these conditions, the activated derivatives (III) are mixed anhydrides of general formula:

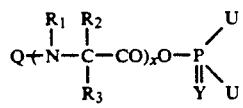

with U being R, —ZR or —N(R)$_2$ and R, Z and Y having the meanings defined above.

The silylation reaction of the acid group is preferably carried out, starting with an N-protected amino acid or peptide, by reaction with a silylating reagent of formula $ASiR_4R_5R_6$ in which the terms A, $R_4$, $R_5$ and $R_6$ have the same meaning as above.

The silylation reaction of the amine group is preferably carried out, starting with an amino acid or peptide, by reaction between a corresponding ester and a silylating reagent of formula $ASiR_4R_5R_6$ in which the terms A, $R_4$, $R_5$, and $R_6$ have the same meaning as above.

These silylation reactions are performed under the conditions known in the prior art.

The amino acid or peptide derivatives are introduced with the silylating agent into a solvent such as, for example, an ether (tetrahydrofuran), a halogenated aliphatic solvent, an ester, a nitrile (acetonitrile) or an amide (DMF).

According to one method, preferably amino acid or peptide concentrations in the solvent of between 0.1 and 1 mole per liter are used.

Concentrations of silylating agent with respect to the amino acid or peptide of between 1 and 3 moles are advantageously used.

In a particulary preferred embodiment of the invention, the second step of bringing a peptide or an amino acid having a protected amine group and an oxygen-silylated acid group into contact with an organic phosphorus derivative is conducted under a stream of inert gas, such as nitrogen or argon, in an aliphatic or aromatic solvent.

Any solvent enabling the activated peptide or amino acid to be solubilized, and which does not react either with the peptide or amino acid or with the phosphorus derivative, may be used. The solvent is chosen, in particular, from methylene chloride, chloroform, 1,2-dichloroethane, chlorobenzene, acetonitrile and tetrahydrofuran.

In a second method of carrying out the process according to the invention, it is also possible, during the activation of the peptide or amino acid by the non-coordinated phosphorus derivative, to add epoxides chosen from 1,2-epoxyalkanes or cycloalkanes to the solution. It is preferable to use 1,2-epoxycyclopentane and 1,2-epoxypropane. In this second method of carrying out the invention, it is preferable to use chloroform or methylene chloride as the solvent. The reaction temperature can vary, in particular, from $-10°$ C. to $30°$ C.

It is preferable to use a quantity of phosphorus derivative such that the mole ratio of the derivative to the amino acid or peptide is between 0.8 and 0.95.

The reaction between the phosphorus-containing derivative and the amino acid or peptide is preferably carried out at a temperature of between $-15°$ C. and $30°$ C. Preferably, the molar concentration of the phosphorus-containing derivative or of the amino acid or peptide in the solvent is between 0.01 and 0.1 mole/liter of solvent.

The time of the activation reaction advantageously varies between 30 minutes and 2 hours according to the first process for carrying out the second step of the invention, and between 10 minutes and 1 hour according to the second process for carrying out the second stage of the invention.

As regards to the condensing or coupling reaction in the third step, it is known in the prior art, such as in European Patent No. 184,243, to couple silyl derivatives to the carboxyl group and to the amine group. However, in none of these processes is there described coupling coupling or condensing between a derivative activated by a phosphorus-containing group and a derivative silylated on the nitrogenous group. In point of fact, this very precise coupling or condensing brings about the altogether unexpected result of no racemization.

The coupling or condensing reaction, or third step of the process of the invention, is carried out by preferably adding the silylated amino compound to the solution of the activated peptide amino acid under an inert gas atmosphere and preferably at a temperature of between $-10°$ C. and $20°$ C. A metal catalyst, chosen from zinc halides, such as zinc chloride or zinc bromide, or copper halides, such as cupric bromide or cupric iodide, is advantageously added.

The time of the condensing or coupling reaction preferably varies between 2 hours and 24 hours.

In another process, an additive is introduced into the reaction medium before the addition of the amino compound. The additive may be, by way of a non-limiting example, chosen from N-hydroxysuccinimide, N-hydroxy-5-norbornene-2,3-dicarboximide, 1-hydroxybenzotriazole and 3,4-dihydro-3-hydroxy-4-keto-1,2,3-benzotriazine. This additive may be used in the form of either a cesium salt, or a tetraalkylammonium salt, or a tetraalkylphosphonium salt.

The invention will be described more fully by means of the examples which follow, which must in no case be considered to limit the invention.

EXAMPLE 1

0.43 g (1.94 mmol) of benzoyl-L-valine and 0.5 g (3.8 mmol) of dimethylsilyldiethylamine were stirred in 20 ml of anhydrous methylene chloride (stabilized by amylene) under nitrogen for 5 hours at room temperature. The reaction mixture was then concentrated under vacuum without heating. The crude benzoyl-L-valine dimethylsilyl ester residue was taken up with 70 ml of methylene chloride. 0.46 g (1.81 mmol) of BOP-Cl was added, which remained in suspension. A partial vacuum was applied for 2 min., and then a strong nitrogen stream was bubbled through the reaction mixture for 45 min. The dimethylsilyl chloride was carried over with part of the solvent, which caused a temperature drop to $-15°$ C. The final volume was adjusted to 35 ml by adding an additional amount of solvent so that the solution was 0.05M. The activating reagent was then completely dissolved. 0.25 g (1.81 mmol) of anhydrous zinc chloride was added and nitrogen was bubbled through for another 2 min. Lastly, 0.36 g (1.81 mmol) of methyl ester of N-trimethylsilyl-L-valine, 0.304 g (3.62 mmol) of 1,2-epoxycyclopentane, and 73 microliters (1.81 mmol) of methanol were added, and the mixture was stirred for 16 hours at room temperature under nitrogen.

0.53 g (1.81 mmol) of the Bz-Val-Gly-OMe dipeptide was then added, which will act as a test for the determination of the yield in high performance liquid chromatography. The reaction mixture was washed 3 times with a normal solution of citric acid, then 3 times with a saturated solution of sodium bicarbonate, and then once with water. The organic phase was dried on magnesium sulfate and the solvent was evaporated off under vacuum.

The yield of Bz-Val-Val-OMe and the degree of racemization, expressed in % DL, were determined from the crude residue by reverse phase high performance liquid chromatography, on a C18 Ultrasphere Altex column, with a mixture of MeOH 52%—H$_2$O 48% as the eluent and a flow rate of 1 ml/min (254 nm detection).

64% yield      DL 0%

EXAMPLE 2

The procedure of Example 1 was followed, but with a condensing or coupling time of 24 hours.

64% yield      DL 1%.

EXAMPLE 3

The procedure of Example 1 was followed, but in 0.2M solution.

68% yield      DL 2.5%.

EXAMPLE 4

The procedure of Example 1 was followed, but without additions of zinc chloride.

50% yield      DL 11.7%.

EXAMPLE 5

0.43 g (1.94 mmol) of benzoyl-L-valine and 0.5 g (3.8 mmol) of dimethylsilyldiethylamine in 20 ml of methylene chloride were stirred under nitrogen for 5 hours at room temperature. The reaction mixture was then concentrated under vacuum without heating. The crude residue was taken up with 70 ml of CH$_2$Cl$_2$. 0.46 g (1.81 mmol) of BOP-Cl was added, a partial vacuum was applied for 2 min., and then a strong nitrogen stream was bubbled through for 45 minutes. The dimethylsilyl chloride was carried over with part of the solvent, which caused a temperature drop to $-15°$ C. The final volume was adjusted to 35 ml (0.05M solution) by adding solvent. 0.25 g (1.81 mmol) of anhydrous zinc chloride was then added and nitrogen was bubbled through for another 2 min. Lastly, 0.36 g (1.81 mmol) of methyl ester of N-trimethyl-silyl-L-proline, 0.304 g (3.62 mmol) of 1,2-epoxy-cyclopentane, and $73 \times 10^{-3}$ ml (1.91 mmol) of methanol were added and the mixture was stirred for 16 hours under nitrogen.

0.53 g (1.81 mmol) of the Bz-Val-Gly-OMe test dipeptide was then added, the reaction mixture was washed 3 times with a 1N solution of citric acid, 3 times with saturated sodium bicarbonate and once with water. The reaction mixture was dried on magnesium sulfate and the solvent was evaporated off under vacuum.

The yield of Bz-Val-Pro-OMe and the degree of racemization (expressed in % DL) were determined from the crude residue by reverse phase high performance liquid chromatography, on a C 18 Ultrasphere Altex column, with a mixture of MeOH 48%—H$_2$O 52% as the eluent and a flow rate of 1 ml/min (254 nm detection).

68% yield      DL 0.2%

EXAMPLE 6

0.43 g of benzoyl-L-valine (1.94 mmol) and 1 ml of hexamethyldisilazane in 20 ml of methylene chloride were stirred under nitrogen for 2 hours at room temperature. The reaction mixture was then concentrated under vacuum without heating. The crude residue of trimethylsilyl ester of benzoyl-L-valine was taken up with 35 ml of methylene chloride. 0.304 g (3.62 mmol) of 1,2-epoxy-cyclopentane and 0.46 g (1.81 mmol) of BOP-Cl were successively added. After 20 min of stirring at room temperature under nitrogen, 0.25 g (1.81 mmol) of anhydrous zinc chloride was introduced, and then, after stirring for 5 min, 0.37 g (1.81 mmol) of methyl ester of N-trimethylsilyl-L-valine and $73 \times 10^{-3}$ ml (1.81 mmol) of methanol were added. The reaction mixture was stirred under nitrogen for 16 hours at room temperature.

The treatment and the analysis by high performance liquid chromatography were carried out as in Example 1:

74% yield        DL 0%

COMPARATIVE EXAMPLE 6

0.46 mg (1.81 mmol) of BOP-Cl and 0.25 ml (1.81 mmol) of triethylamine were added successively at −30° C. to 40 mg (1.81 mmol) of benzoyl-L-valine dissolved in 20 ml of anhydrous methylene chloride. After stirring for 15 minutes at this temperature, 0.37 g (1.81 mmol) of the methyl ester of benzoyl-L-valine and 0.25 ml (1.81 mmol) of triethylamine were added. The reaction mixture was allowed to return to room temperature and stirring was continued for 15 hours. The reaction mixture was then washed 3 times with 1N citric acid, 3 times with a saturated solution of sodium bicarbonate, and finally with water. The organic phase was dried on magnesium sulfate and the solvent was evaporated off under vacuum.

60% yield        Total racemization.

EXAMPLE 7

0.63 g (1.94 mmol) of the beta-benzyl ester of N-tert-butyloxycarbonyl-L-aspartic acid and an excess of hexamethyldisilazane in 20 ml of $CH_2Cl_2$ were stirred under nitrogen for 2 hours at room temperature. The reaction mixture was concentrated under vacuum without heating and the residue was taken up with 36 ml of methylene chloride. 0.304 g (3.62 mmol) of 1,2-epoxycyclopentane was then added followed by the addition of 0.46 g (1.81 mmol) of BOP-Cl. After stirring for 20 min at room temperature under nitrogen, 0.25 g (1.81 mmol) of zinc chloride was introduced. After stirring for 5 min at room temperature, 0.46 g (1.81 mmol) of methyl ester of N-trimethylsilyl-L-phenylalanine and $73 \times 10^{-3}$ ml (1.81 mmol) of methanol were added and the mixture was stirred for 16 hours at room temperature under nitrogen.

The mixture was washed successively 3 times with 1N citric acid, 3 times with a saturated solution of sodium bicarbonate and once with water. The mixture was then dried on magnesium sulfate. The solvent was evaporated off under vacuum.

The yield of BOC-Asp(OBzl)-Phe-OMe was 50%. Oil was defined by its NMR spectrum and by its mass spectrum.

Cleavage of the protecting group to release Aspartame was finally carried out according to the procedures of the art.

EXAMPLE 8

0.43 g of benzy-L-valine (1.94 mmol) and 1 ml of hexamethyl-disilazane in 20 ml of methylene chloride were stirred under nitrogen for 2 hours at room temperature. The reaction mixture was then concentrated under vacuum without heating. The crude residue of trimethylsilyl ester of benzoyl-L-valine was taken up with 35 ml of methylene chloride. 0.304 g (3.62 mmol) of 1,2-epoxy-cyclopentane and 0.43 g (1.81 mmol) of commercial Dpp-Cl containing 2% of diphenylphosphinic acid were successively added. After stirring for 20 min at room temperature under nitrogen, 0.41 g (1.81 mmol) of dry cupric bromide was introduced into the solution. After stirring for 5 min, 0.36 g (1.81 mmol) of methyl ester of N-trimethylsilyl-L-proline and 0.304 g (3.62 mmol) of 1,2-epoxy-cyclopentane were added.

The reaction mixture was finally stirred for 16 hours under nitrogen at room temperature.

70% yield        DL 1.3%

EXAMPLE 9

The procedure of Example 8 was followed, but cupric bromide was replaced by zinc bromide (1.81 mmol).

67% yield        DL 0.7%

EXAMPLE 10

The procedure of Example 8 was followed, but dry cupric iodide was used (1.81 mmol).

82% yield        DL 0.9%

EXAMPLE 11

An aqueous solution of 3 g (9.2 mmol) of cesium carbonate was gradually added to a solution of 3 g (18.4 mmol) of 3,4-dihydro-3-hydroxy-4-ceto-1,2,3-benzotriazine in 20 ml of distilled water and 20 ml of ethanol. The reaction mixture was then concentrated to dryness under vacuum and the yellow residue was dried by azeotropic distillation. A 90% yield was achieved.

The procedure of Example 1 was followed, starting from 0.43 g (1.94 mmol) of benzoyl-L-valine and 0.43 g of DppCl (1.81 mmol) but substituting the addition of zinc chloride by that of 0.53 g (1.81 mmol) of the cesium salt of 3,4-dihydro-3-hydroxy-4-keto-1,2,3-benzotriazine. The reaction mixture was stirred under nitrogen for 15 minutes while allowing the temperature to return to 0° C. 0.36 g (1.81 mmol) of the methyl ester of N-trimethyl-silyl-L-valine was then added and the mixture stirred for 2 hours at room temperature under nitrogen.

Quantitative yield        DL 0.2%

While particular embodiments of the invention have been described, it will be understood that the invention is not so limited since many modifications and variations could be made without departing from the spirit or scope of the invention.

What is claimed is:

1. A process for preparing an optically active peptide synthon, comprising the steps of:
   (a) preparing an oxygen-silyl derivative of a peptide or an amino acid in which the alpha-amino group of the amino acid or the amino terminus of the peptide is protected;
   (b) activating the oxygen-silyl peptide or amino acid with a halogenated phosphorus derivative; and
   (c) condensing the activated peptide or amino acid with a peptide or an amino acid having a protected acid group and an N-silylated amine group to obtain a peptide synthon, wherein steps (a), (b) and (c) are performed in the substantial absence of a base.

2. The process of claim 1, wherein the peptide synthon is substantially optically pure.

3. The process of claim 2, wherein a metal halide catalyst is used during the third step.

4. The process of claim 3, wherein said metal halide is zinc chloride, zinc bromide, cupric iodide, or cupric bromide.

5. The process as claimed in claim 1, wherein the peptide synthon activated by the phosphorus derivative contains more than one amino acid.

6. The process as claimed in claim 1, wherein the phosphorus derivative is selected from the group consisting of:

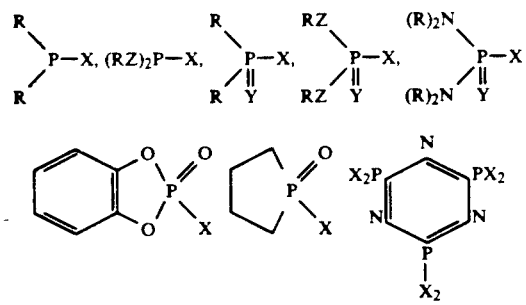

in which:
- X is selected from the group consisting of chlorine and bromine,
- R denotes an alkyl group $C_nH_{2n+1}$ with n being an integer between 1 and 4, a phenyl group, or a 2-oxo-3-oxazolidinyl group, and
- Z and Y are independently oxygen or sulfur atoms.

7. The process as claimed in claim 6, wherein the phosphorus derivative is selected from the group consisting of diphenylphosphinyl chloride (Dpp-Cl) and N,N'-bis(2-oxo-3-oxazolidinyl)-phosphinyl chloride (BOP-Cl).

8. The process as claimed in claim 1, wherein the second step is carried out under a stream of inert gas and in the presence of an aliphatic or aromatic solvent.

9. The process as claimed in claim 8, wherein the solvent is selected from the group consisting of methylene chloride, chloroform, 1,2-dichloroethane, chlorobenzene, acetonitrile and tetrahydrofuran.

10. The process as claimed in claim 1, wherein the second step is carried out at a temperature between $-15°$ C. and $30°$ C.

11. The process as claimed in claim 8, wherein the second step is carried out at a temperature between $-15°$ C. and $30°$ C.

12. The process as claimed in claim 1, wherein, during the second step, the mole ratio of the phosphorus derivative to the amino acid or peptide is between 0.8 and 0.95.

13. The process as claimed in claim 1, wherein the second step is carried out in the presence of a solvent and the amino acid or peptide is present in the solvent in an amount between 0.01 and 0.1 mole/liter solvent.

14. The process as claimed in claim 8, wherein the amino acid or peptide is present in the solvent in an amount between 0.01 and 0.1 mole/liter solvent.

15. The process as claim in claim 1, wherein the second step further comprises the presence of at least one epoxide selected form the group consisting of 1,2-epoxyalkanes and cycloalkanes.

16. The process as claimed in claim 15, wherein the second step is carried out in the presence of a solvent selected from the group consisting of chloroform and methylene chloride.

17. The process as claimed in claim 1, wherein, during the third step, a cesium salt, a tetraalkylammonium salt or a tetraalkylphosphonium salt of an additive selected from the group consisting of N-hydroxysuccinimide, N-hydroxy-5-norbornene-2,3-dicarboximide, 1-hydroxybenzotriazole and 3,4-dihydro-3-hydroxy-4-keto-1,2,3-benzotriazine is added.

18. The process of claim 1, wherein the halogenated phosphorus derivative is non-coordinated.

* * * * *